United States Patent [19]

Gozzo et al.

[11] 4,390,705

[45] Jun. 28, 1983

[54] FUNGICIDAL N-SUBSTITUTED ETHYLENDIAMINO-DITHIOCARBAMATES WHICH DO NOT GIVE RISE TO THE FORMATION OF ETHYLENTHIOUREA

[75] Inventors: Franco Gozzo, Saronno; Nicola Troiani, Milan; Simone Lorusso, S. Giuliano Milanese; Romano Santi, Florence, all of Italy

[73] Assignee: Montedison S.p.A., Milan, Italy

[21] Appl. No.: 343,861

[22] Filed: Jan. 29, 1982

Related U.S. Application Data

[63] Continuation of Ser. No. 114,510, Jan. 23, 1980, abandoned, which is a continuation of Ser. No. 817,821, Jul. 21, 1977, abandoned.

[30] Foreign Application Priority Data

Jul. 22, 1976 [IT] Italy .............................. 25587 A/76

[51] Int. Cl.³ .................. C07D 333/48; C07C 143/00; A01N 55/02; A01N 47/10

[52] U.S. Cl. .................................... 549/3; 260/501.12; 260/513.5; 260/429.9; 260/438.1; 424/245; 424/286; 424/289

[58] Field of Search ............. 260/501.12, 513.5, 429.9, 260/438.1; 549/68, 3

[56] References Cited

U.S. PATENT DOCUMENTS 4,079,146 3/1978 Miller et al. ..................... 260/513.5

FOREIGN PATENT DOCUMENTS 925074 5/1963 United Kingdom ............. 260/513.5

*Primary Examiner*—Alan Siegel

[57] ABSTRACT

There are disclosed new fungicidally active N-substituted ethylendiamino-dithiocarbamates, in particular such dithiocarbamates which are active against *Plasmopara viticola* infections (B. et C.) Berl. et de Toni (Peronoapora of the vine) and against infections by other fungi that are noxious to useful agricultural cultivations. An important characteristic of the new fungicidally active dithiocarbamates of the invention is that use thereof does not result in the formation of ethylenthiourea.

7 Claims, No Drawings

FUNGICIDAL N-SUBSTITUTED ETHYLENDIAMINO-DITHIOCARBAMATES WHICH DO NOT GIVE RISE TO THE FORMATION OF ETHYLENTHIOUREA

This is a continuation of application Ser. No. 114,510, filed Jan. 23, 1980, abandoned, which in turn is a continuation of application Ser. No. 817,821 filed July 21, 1977 and now abandoned.

THE PRIOR ART

Ethylen-bis-dithiocarbamates of the formula

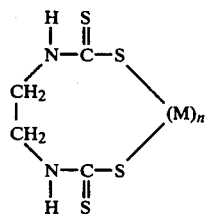

in which M is an alkaline metal, e.r., Zn, Mn, have been known to be fungicidally active for some time and have been used to protect plants from the attack of pathogenous fungi.

Recently, that family of fungicides has been placed in the control of health authorities in different countries of the world because ethylenthiourea is set free, in time, from the ethylenbis-dithiocarbamates, and ethylenthiourea has come under serious suspicion as a health hazard.

THE PRESENT INVENTION

One object of this invention is to provide new products which have the same fungicidal activity as the prior art ethylendis-dithiocarbamates, but which do not give rise to the evolution of the potentially harmful ethylenthiourea.

Another object of the invention is to provide methods for preparing the new fungicides of the invention.

Still another, and more specific, object of the invention is to provide new fungicidal compounds which exert fungicidal activity against the main plant disease for combatting which, the only agents available at the present time are the potentially damaging ethylenbis-dithiocarbamates, e.g., the peronospora of the vine (Plasmopora viticola).

These and other objects which will appear hereinafter are achieved by the invention which provides new compounds having the general formula (I) as follows:

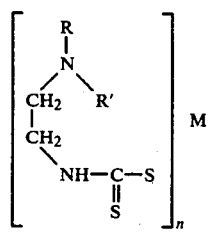

in which
R is H or

and when
R is N, R' is an alkyl containing from 1 to 12 carbon atoms and which can be linear or branched; phenyl or benzyl; alkenyl, substituted alkenyl, alkinyl, substituted alkinyl having from 2 to 5 C, acyl; $SO_2''$, 3-sulpholanyl;

in which R'' is alkyl having from 1 to 6 C or phenyl or benzyl and when R is

R' is alkyl containing from 1 to 12 C and linear or branched; phenyl or benzyl; alkenyl; substituted alkenyl; alkinyl; substituted alkinyl all having from 2 to 5 C; or 3-sulpholanyl;

M is H, when R' is not alkyl; or an alkaline metal selected from the group consisting of Zn, Mn and Cu; and n is 1 or 2 depending on the valency of the metal M.

The compounds of general formula I in which R is alkyl, aryl, alkenyl, alkinyl, acyl, or $SO_2R''$ is H are prepared by the following sequence of reactions, the first of which consists of condensing an excess of ethylendiamine with R'-X, X being a halogen.

The two reactants are used in proportions of at least 2 mols of ethylendiamine per mole of R'-X. The reaction proceeds as in (2) below:

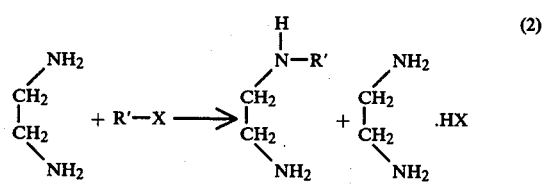

The intermediate, $R'NH-CH_2-CH_2-NH_2$, isolated from the reaction mixture, is then reacted with 1.0 mole of carbon sulphide under one of the following conditions and depending on the end product desired:

(a) in an alcohol medium, with separation of the precipitate formed during the reaction;

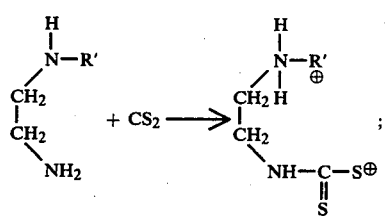

(b) in an aqueous medium, in the presence of $CS_2$ and an alkali metal hydroxide, to obtain a product of formula (I) in which M is an alkali metal:

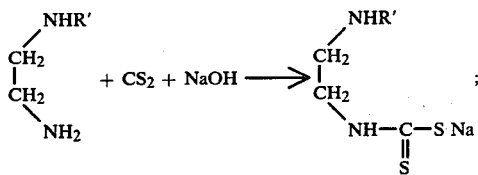

(c) in an aqueous medium as in (b) but followed by the addition of an inorganic salt of a metal such that a product of formula (I) is obtained, in which M is a non-alkaline metal.

To obtain compounds of general formula (I) in which R is hydrogen and R' is acyl, introduction of the acyl group is accomplished by condensing an excess of the ethylendiamine with an acyl halide or by reacting an excess of the diamine with an ester comprising an acyl group according to the following reaction:

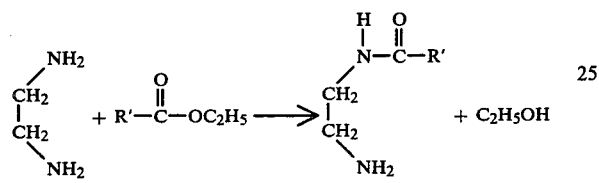

In preparing compounds of general formula (I) in which R is hydrogen and R' is 3-sulpholanyl, the latter group can be introduced by adding 3-sulpholene to an excess of the ethylendiamine according to the following equation:

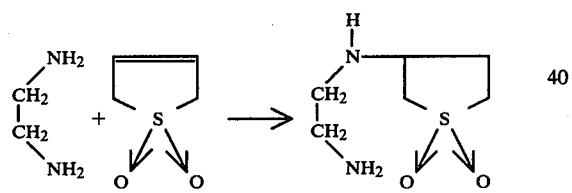

In preparing compounds of general formula (I) in which R is H and R' is

R" being alkyl or aryl, the introduction of the latter group can be achieved by adding a selected and suitable iso-thiocyanate to an excess of the ethylendiamine, the reaction proceeding as follows:

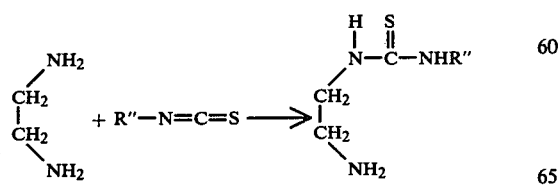

In preparing the compounds of the invention, and of general formula (I), in which R is

the processes described under (b) and (c) above can be used, using 2.0 moles of CS$_2$ per mole of the R'-NH-CH$_2$-CH$_2$-NH$_2$ intermediate.

The following compounds have been found to be particularly efficacious in preventing infection of plants by Peronospora:

(1) The inner salt of N-(2'-allylaminoethyl)dithiocarbamic acid of the formula:

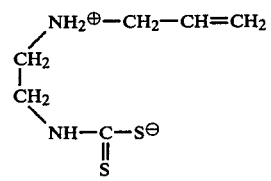

having a m.p. of 125° C., with decomposition, applicants' code number 7906; and the zinc salt thereof, applicants' code number 7907.

(2) Zinc N(2'-sec.butyl-aminoethyl)dithiocarbamate of the formula:

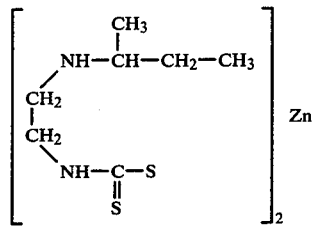

(applicants' code No. 7928)

(3) Zinc N(2'-sec.pentyl-aminoethyl)-dithiocarbamate of the formula:

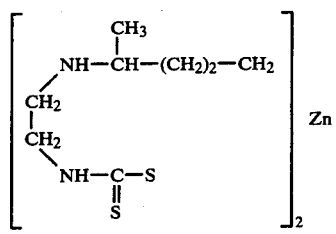

(applicants' No. 7932)

(4) Zinc N-(acetylamino-ethyl)-dithiocarbamate of the formula:

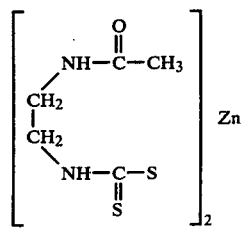

-continued (applicants' No. 7931)

(5) Zinc N-(3'sulpholanyl-ethyl)dithiocarbamate of the formula:

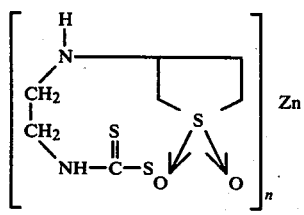

(applicants' No. 8046)

(6) Zinc N(2'-sec.butylamino)ethylenbisdithiocarbamate of the following formula:

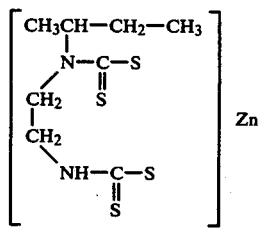

(applicants' code No. 5330/2)

Compounds (1) to (6) have been tested not only with regard to the activity thereof against the Peronospora (see Ex. 5 infra), but have also been tested as described in Example 4 in order to check the absence of any significant quantity of ethylenthiourea (ETU) among the decomposition products.

The compounds according to this invention may be suitably formulated to yield wettable powders by using fillers such as: kaolin, diatomite, etc., in the presence of wetting, dispersing and suspending agents.

There may also be used dispersing powders such as talcum powder, etc., and the products so obtained can be used as such.

The following examples are given to illustrate the invention in more detail and are not intended to be limiting.

EXAMPLE 1

Preparation of salts derived from N-(2'-allylamino-ethyl)dithiocarbamic acid

The N-allyl ethylendiamine intermediate was prepared according to the following method, described hereinabove:

76.5 g of allyl chloride (1 mole) were slowly mixed with 264 g of ethylendiamine (4.4 moles). The resulting solution was reflux-heated for ½ an hour and then distilled at room pressure. The fraction comprised between boiling points 117° and 140° C. was gathered and subjected to fractional distillation to obtain 27.2 g of N-allylethylendiamine having a b.p. of 156°–158° C. [J.A.C.S. 67, 1581 (1945)].

Preparation of the internal salt of N-(2'-allylaminoethyl)dithiocarbamic acid (N 7906)

To 10 g of N-allylethylendiamine (0.1 moles) dissolved in 50 cc of ethanol there were admixed, under stirring, 7.6 g of CS$_2$ (0.1 moles) dissolved in 50 cc ethanol, the temperature being maintained at about 5° C. Once the addition is accomplished, stirring is continued for another 15 minutes, after which the resulting precipitate is filtered and, after washing with ethanol, consists of 15.6 g of white crystals having a m.p. of 125° C. (with decomposition) of N-(2'-allylaminoethyl)dithiocarbamic acid having the following structure of an internal salt:

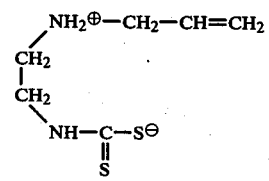

| Elementary analysis: | |
|---|---|
| Theoretical % | Found % |
| C = 40.88% | 41.07% |
| H = 6.86% | 6.88% |
| N = 15.89% | 15.96% |

Preparation of zinc-N-(2'-allylaminoethyl)-dithiocarbamate (N 7907)

To 17.6 g of N 7906, internal salt (0.1 moles) dissolved in 100 cc of a solution of 1 N, of NaOH (0.1 moles), there were mixed, under stirring, 7.5 g of ZnCl$_2$ (0.055 moles) dissolved in 50 cc of water. The precipitate thus formed was then filtered and washed with water, in order to yield, after drying, 19 g of zinc-N-(2'-allylaminoethyl)-dithiocarbamate, at a titer of 91%, determined on the basis of the CS$_2$ content according to the method described by Clarke et al, Analytical Chemistry, 23, 1846 (1951), modified according to Unichim Handbook No. 78.

EXAMPLE 2

Preparation of the salts of N(2'-alkylaminoethyl)-dithiocarbamic acids

The N-sec.butyl-ethylendiamine intermediate was prepared by the following method: to 300 g of ethylendiamine (5 moles), heated to 60° C., were admixed 137 g of 2-bromobutane (1 mole), under constant stirring. On completion of the addition, the reaction mixture was heated to 90° C. and maintained at that temperature for 15 minutes.

After cooling down, the two phases that had formed were separated. The lower phase was extracted with diethylether and the ether extract was mixed with the upper phase. After removal of the solvent, the residue was distilled under reduced pressure in order to yield 80 g of N-sec.butyl-ethylendiamine with b.p. (at 15 mmHg) of between 64° and 66° C. and with a gaschromatographic titer of 97%.

Preparation of
zinc.N-(2'sec.butylaminoethyl)-dithiocarbamate (N 7928)

To a mixture of 11.6 g of N-sec.butylethylendiamine (0.1 moles) and 100 cc of solution of 1 N of NaOH (0.1 moles), heated to 35° C., in 45 minutes there were added 7.6 g of CS₂ (0.1 moles). Once the addition had been completed, the temperature reached was maintained at that level for another 30 minutes.

After cooling, there were added 7.5 g of ZnCl₂ (0.055 moles) dissolved in 100 cc of water. The precipitate thus formed was then filtered and washed with water so that, after drying, there were obtained 17 g of zinc N-(2'-sec.-butylaminoethyl)-dithiocarbamate with a titer of 95%, determined by the modified Clarke method.

Preparation of
zinc.N-(2'-sec.pentylaminoethyl)-dithiocarbamate (N 7932)

By operating according to the above described process, preceded by the preparation of intermediate N-sec.pentylethylendiamine, there was prepared the zinc N-(2'-sec.pentylaminoethyl)-dithiocarbamate, at a titer of 88% determined by the modified Clarke method.

EXAMPLE 3

Preparation of
zinc.N-(2'-acetylaminoethyl)-dithiocarbamate

The N-acetylethylendiamine intermediate was prepared according to the method already described and as follows:

To 258 g of an aqueous solution of ethylendiamine at 70% concentration (3 moles), there were admixed 89 g of ethyl acetate (1 mole) at room temperature, and the mixture was maintained under stirring until it was completely homogenous. After 48 hours, the solution was distilled at reduced pressure, thereby gathering the fraction with the boiling point comprised between 115° and 130° C. (5 mm Hg), re-distillation of which gave 61 g of monoacetylethylendiamine with a b.p. (at 5 mm Hg) of 125° to 130° C.

Preparation of
zinc.N-(2'-acetylaminoethyl)-dithiocarbamate (N 7931)

By operating according to the process described in Example No. 2, starting from 10.2 g of N-acetyl-ethylendiamine, there were obtained 15 g of zinc N-(2'-acetylaminoethyl)-dithiocarbamate having titer of 96%, determined according to the modified Clarke method.

EXAMPLE 4: (Determination of ETU)

30 mg of the sample under examination were placed in a conical flask provided with a reflux cooler and mixed with 50 g of distilled water. The mixture was then reflux-heated for 15 minutes.

After cooling down, the content of ethylenthiourea in water was determined by chromatography on thin layer according to the methodology described by G. Gzegledi-Janko; Journal of Chromatography 31, 89 (1967). The method used allows a precision in measurement of 5–10%, with limits of sensitivity of about 0.03%.

For comparative purposes, one of the samples subjected to the ethylenthiourea formation test consists of Zineb (Zn ethylenbisdithiocarbamate).

On all the samples examined, the Zineb included, there was also determined the content in ethylenthiourea before the heating, by subjecting said samples to extraction with methanol (8 cc of methanol for 0.5 g of sample) and then using the Gzegledi-Janko methodology. The following results were achieved:

| Mark of Sample | Formula | % BTU Initial | % BTU After heating |
|---|---|---|---|
| Zineb reference compound | ![structure with NH—C(=S)—S—Zn—S—C(=S)—NH linked by ethylene] | 0.8 | 15–20 |
| M 7907 | [NH—CH₂CH=CH₂ / NH—C(=S)—S]₂ Zn | 0.1 | 0.5 |
| 7928 | [NH—CH(CH₃)—CH₂—CH₃ / NH—C(=S)—S]₂ Zn | <0.03 | abt. 0.1 |
| 7931 | [NH—C(=O)—CH₃ / NH—C(=S)—S]₂ Zn | <0.03 | <0.03 |
| 7932 | [NH—CH(CH₃)—(CH₂)₂—CH₃ / NH—C(=S)—S]₂ Zn | 0.04 | 0.1 |

EXAMPLE 5

Preventive activity on Peronospora of vine (*Plasmopara viticola* (B. et C.) Berl et de Toni)

The vine leaves ov. Dolcetto, grown in pots in an environment conditioned at 25° C. and for a relative humidity rate of 60%, were treated by sprinkling both leaf faces with the products under examination in a hydroacetonic solution (20% of acetone vol/vol).

At different time intervals from the treatment, the leaves were sprinkled on their lower leaf face with an aqueous suspension of conidia of *Plasmopara viticola* (200,000 conidia/cc); after 24 hours resting in a humidity saturated environment at 21° C., the plants were transferred to a 70% R.H. at 21° C., for a period of incubation (7 days). At the end of the incubation period the intensity of the infection was evaluated by means of indexes of an evaluation scale ranging from 100 (healthy plants) to 0 (completely infected plant).

The results of the preventive activity are recorded in the following table:

| Formula | Mark of Sample | Dose % | % Activity Infection after 1 day from treatment | % Activity Infection after 4 days from treatment |
|---|---|---|---|---|
| (structure) | Zincb (reference compound) | 2 | 100 | 97 |
|  |  | 1 | 100 | 65 |
| (structure) | M 7906 | 2 | 100 | 98 |
|  |  | 1 | 100 | 62 |
| (structure) | M 7907 | 2 | 100 | 81 |
|  |  | 1 | 99 | 69 |
| (structure) | M 7928 | 2 | 97 | — |
|  |  | 1 | 86 | — |
| (structure) | M 7931 | 2 | 95 | — |
|  |  | 1 | 93 | — |
| (structure) | M 7932 | 2 | 100 | — |
|  |  | 1 | 89 | — |

We claim:

1. An antifungin selected from the group consisting of ethylendiamino-dithiocarbamic acid salts in which at least one of the hydrogen atoms bound to the nitrogen atom in the amino group of ethylendiamino mono- or bis-dithiocarbamate is substituted, said antifungin having the general formula (I):

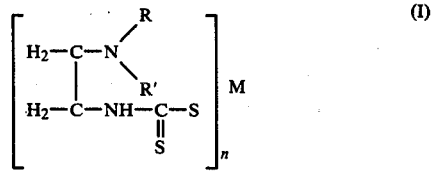

in which

R is selected from the group consisting of H and

R' is selected from the group consisting of $C_1$–$C_{12}$ alkyl, $C_2$–$C_{12}$ alkenyl or alkinyl, $C_2$–$C_{12}$ acyl and a sulpholanyl group;

M is selected from the group consisting of Cu, Zn and Mn; and n is 1 or 2 depending on the valence of M; and the internal salts of the acids comprehended in formula (I), said antifungin being further characterized in that it does not form ethylenthiourea or substituted ethylenthioureas on standing or under heating.

2. An antifungin which is the internal salt of N(-2'-allylaminoethyl)-dithiocarbamic acid of the formula:

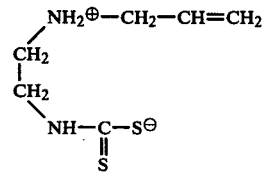

and having a melting point of 125° C. (dec).

3. An antifungin which is zinc N(2'-allylaminoethyl)-dithiocarbamate of the formula:

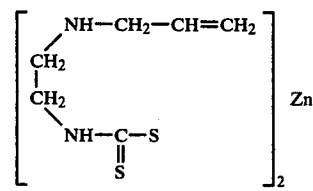

4. A compound according to claim 1, and which is zinc N-(2'-sec.butylaminoethyl)dithiocarbamate of the formula:

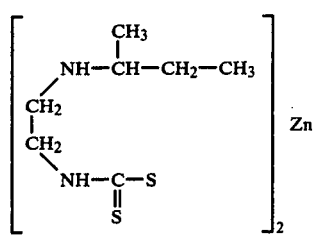
5. An antifungin which is zinc N-(acetylaminoethyl)-dithiocarbamate of the formula
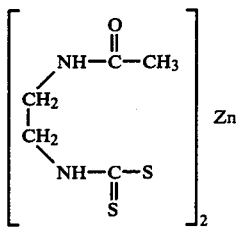
6. An antifungin which is zinc N(-3'-sulpholanylaminoethyl)-dithiocarbamate of the formula
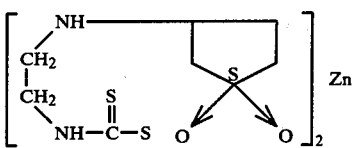
7. A compound according to claim 1, and which is zinc N-(2-sec.butylamino)-ethylen-bis-dithiocarbamate of the formula:
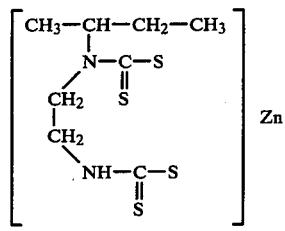
* * * * *